(12) United States Patent
Qasaimeh et al.

(10) Patent No.: US 11,737,452 B2
(45) Date of Patent: Aug. 29, 2023

(54) SYSTEM AND METHOD FOR PAPER-BASED CRYOPRESERVATION

(71) Applicant: New York University in Abu Dhabi Corporation, Abu Dhabi (AE)

(72) Inventors: Mohammad A. Qasaimeh, New York, NY (US); Roaa Alnemari, New York, NY (US)

(73) Assignee: New York University in Abu Dhabi corporation, Abu Dhabi (AE)

(*) Notice: Subject to any disclaimer, the term of this patent is extended or adjusted under 35 U.S.C. 154(b) by 552 days.

(21) Appl. No.: 16/616,665

(22) PCT Filed: Jun. 13, 2018

(86) PCT No.: PCT/US2018/037347
§ 371 (c)(1),
(2) Date: Nov. 25, 2019

(87) PCT Pub. No.: WO2018/231993
PCT Pub. Date: Dec. 20, 2018

(65) Prior Publication Data
US 2021/0169070 A1   Jun. 10, 2021

Related U.S. Application Data

(60) Provisional application No. 62/519,626, filed on Jun. 14, 2017.

(51) Int. Cl.
*A01N 1/02* (2006.01)
*C12M 1/00* (2006.01)
(Continued)

(52) U.S. Cl.
CPC .......... *A01N 1/0231* (2013.01); *C12M 45/22* (2013.01); *A01N 1/02* (2013.01); *C12M 45/00* (2013.01);
(Continued)

(58) Field of Classification Search
CPC ....... A01N 1/0231; A01N 1/02; C12M 45/22; C12M 45/00; C12N 5/0068; C12N 5/0693; G01N 33/50
See application file for complete search history.

(56) References Cited

U.S. PATENT DOCUMENTS

2003/0118982 A1   6/2003   Yamamoto et al.
2009/0325216 A1   12/2009  Mayer
(Continued)

FOREIGN PATENT DOCUMENTS

CA   2974276    8/2016
CN   101381676  6/2011
(Continued)

OTHER PUBLICATIONS

Ivascu et al. Rapid Generation of Single-Tumor Spheroids for High-Throughput Cell Function and Toxicity Analysis. Journal of Biomolecular Screening (2006), 922-932. (Year: 2006).*
(Continued)

*Primary Examiner* — Sean C. Barron
(74) *Attorney, Agent, or Firm* — Fay Kaplun & Marcin, LLP

(57) ABSTRACT

A system and method for cryopreservation of cells or spheroids of cells including obtaining a suspension of the isolated mammalian cells in a medium; applying the suspension to a fibrous substrate comprising a network of interconnected cellulosic fibers defining a plurality of pores therein and allowing the suspension to absorb into the fibrous substrate such that the isolated mammalian cells penetrate and settle to an interior of the fibrous substrate; and cooling the fibrous substrate to or below a temperature of $-80°$ C.

18 Claims, 12 Drawing Sheets

(51) Int. Cl.
*G01N 33/50* (2006.01)
*C12N 5/00* (2006.01)
*C12N 5/09* (2010.01)

(52) U.S. Cl.
CPC .......... *C12N 5/0068* (2013.01); *C12N 5/0693* (2013.01); *G01N 33/50* (2013.01)

(56) References Cited

U.S. PATENT DOCUMENTS

| | | | |
|---|---|---|---|
| 2016/0116454 A1 | 4/2016 | Brockbank et al. | |
| 2017/0009209 A1 | 1/2017 | Kidoaki et al. | |
| 2017/0311587 A1* | 11/2017 | Matsuzawa | A61J 3/00 |
| 2018/0042220 A1 | 2/2018 | Miyagawa et al. | |

FOREIGN PATENT DOCUMENTS

| | | | | |
|---|---|---|---|---|
| JP | 2005040073 A | * | 2/2005 | ............ C12M 45/22 |
| JP | 2017060457 | | 3/2017 | |
| WO | 2009/120963 | | 10/2009 | |
| WO | 2014/105581 | | 7/2014 | |
| WO | WO-2016063806 A1 | * | 4/2016 | ............ A01N 1/021 |
| WO | WO-2016065363 A1 | * | 4/2016 | ............ A01N 1/0205 |
| WO | 2016/112172 | | 7/2016 | |

OTHER PUBLICATIONS

Ng et al. Paper-based cell culture platform and its emerging biomedical applications. Materials Today (Jan.-Feb. 2017), 20(1), 32-44. (Year: 2017).*

Ng et al., "Paper-based Cell Culture Platform and its Emerging Biomedical Applications", Materials Today, vol. 20, No. 1, 2017, pp. 32-44.

Popa et al., "Cryopreservation of Cell Laden Natural Origin Hydrogels for Cartilage Regeneration Strategies", Soft Matter, vol. 9, No. 3, 2013, pp. 875-885.

Derda et al. "Paper-supported 3D cell culture for tissue-based bioassays", PNAS, vol. 106, No. 44, Nov. 2009, pp. 18457-18462.

Ozaki et al., "Self-driven perfusion culture system using a paper-based double-layered scaffold", Biofabrication, vol. 8 No, 3, Aug. 2016, pp. 1-11.

Lee et al., "An efficient and mass reproducible method for vitrifying mouse embryos on a paper in cryotubes", Cryobiology, vol. 66, Mar. 2013, pp. 311-317.

Kim et al., "Successful vitrification of bovine blastocysts on paper container", Theriogenology, vol. 78, May 2012, pp. 1085-1093.

Ehrhart et al., "A comparative study of freezing single cells and spheroids: Towards a new model system for optimizing freezing protocols for cryobanking of human tumours", Cryobiology, vol. 58, Nov. 2009, pp. 119-127.

* cited by examiner

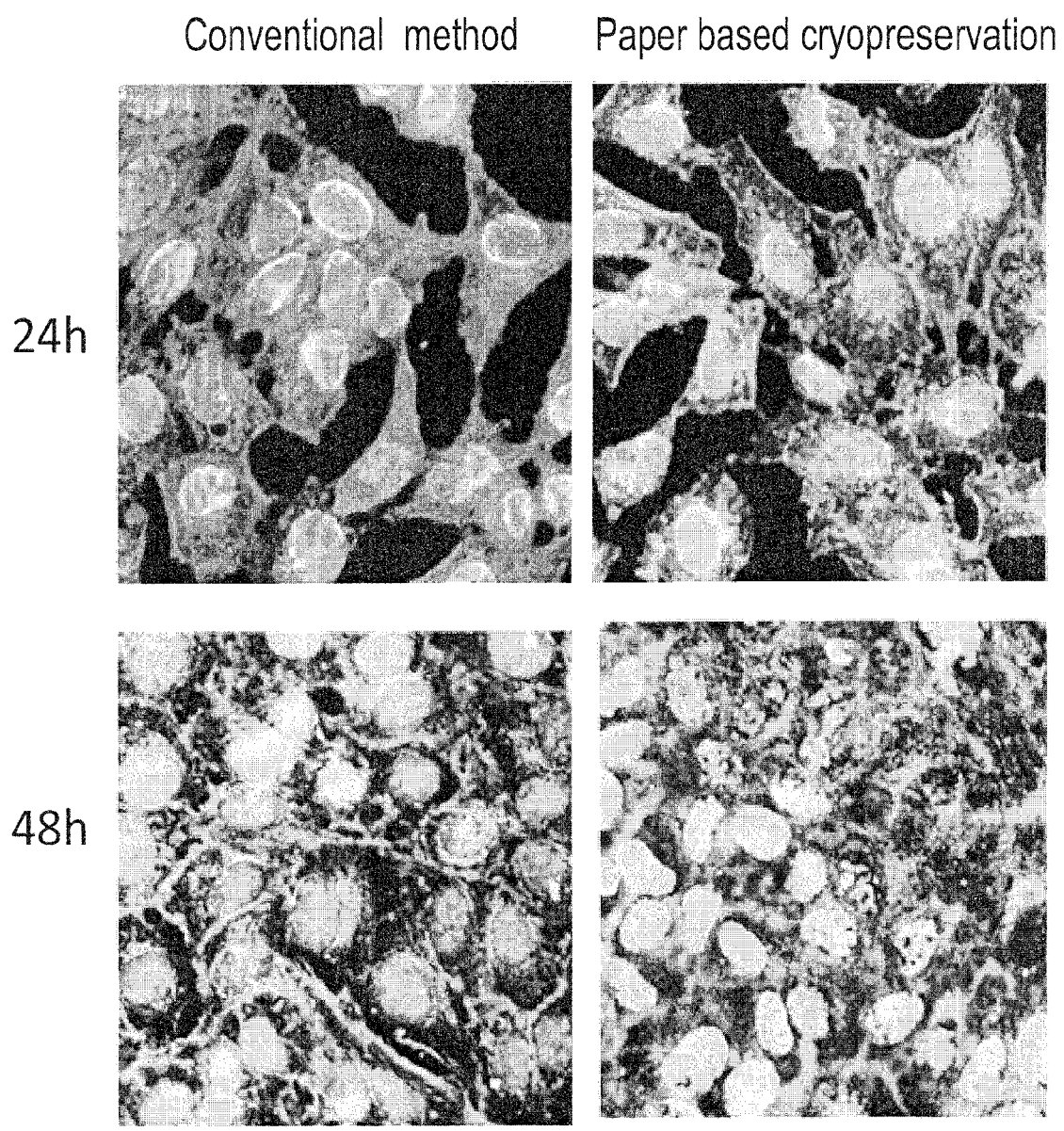
F I G. 6

SYSTEM AND METHOD FOR PAPER-BASED CRYOPRESERVATION

PRIORITY CLAIM

The present application is a National Phase Application of PCT Patent Application Serial No. PCT/US2018/037347 filed on Jun. 13, 2018 which claims priority to U.S. Provisional Application Ser. No. 62/519,626 entitled "System and Method for Paper-Based Cryopreservation" filed on Jun. 14, 2017, the entire contents of the above applications which is hereby incorporated by reference herein.

BACKGROUND

Since the 1960s, cryopreservation to very low temperatures is the main tool to preserve structurally intact living cells and tissues for years. Cryoprotectants, such as glycerol and dimethyl sulfoxide (DMSO), are essential to achieve successful non-lethal cryopreservation by reducing the amount of ice crystals formed during freezing process (vitrification). Traditionally, freezing living cells is achieved by suspending cells in cell culture solution mixed with cryoprotective agent(s), that is later stored in liquid nitrogen. Biotechnology companies claim that they face some difficulties in maintaining cell line banks and exchanging cell line samples, one of which is that storing cells in small vials is space-consuming, labor intensive, with high chance of mixing misplacing. On the other hand, freezing cells in large containers may expose cells to contamination and serious cell damage with every thawing step; thawing the whole container to retrieve a small sample to a customer is thus not a practical way.

Therefore, there is a need for an improved system and method for cryopreservation of cell or multi-cellular aggregates that allows for more efficient storage and maintenance while being easily retrievable in desired quantities while reducing contamination risks and cellular damage as compared to conventional storage methods that require repeated freezing and thawing cycles of an entire stock of cryopreserved cells every time sample is retrieved.

SUMMARY OF THE INVENTION

In accordance with the foregoing objectives and others, one embodiment of the present invention provides a method for cryopreservation of mammalian cells. The method comprises obtaining a suspension of the isolated mammalian cells in a cryopreservation medium comprising a cryoprotectant. In some embodiments, the cryopreservation medium may comprise a hydrogel. In other embodiments, the cryopreservation medium may be substantially free of a hydrogel. The cryoprotectant may be selected from a group consisting of glycerol, dimethyl sulfoxide (DMSO), and a combination thereof. The method also comprises applying the suspension to a fibrous substrate (e.g., paper) comprising a network of interconnected cellulosic fibers defining a plurality of pores therein by allowing the suspension to absorb into the fibrous substrate such that the isolated mammalian cells penetrate, and may settle to or adhere to an interior of the fibrous substrate. In one exemplary embodiment, an average diameter of the plurality of pores may be from about 50 μm to about 150 μm. The method further comprises cooling the fibrous substrate to or below a temperature of −80° C. In some embodiments, the fibrous substrate may also comprise a protein of an extracellular matrix, such as a glycoprotein of the extracellular matrix (e.g., fibronectin). In other embodiments, the fibrous substrate may comprise a chemically stable resin.

In another aspect of the present invention, a system for cryopreservation of mammalian cells is provided. The system comprises a fibrous substrate comprising a network of interconnected cellulosic fibers defining a plurality of pores therein. The fibrous substrate may be configured to absorb a suspension of the isolated mammalian cells therein such that the isolated mammalian cells penetrate, and may settle to or adhere to an interior of the fibrous substrate. In one exemplary embodiment, the substrate may be a roll of paper. The system further comprises a container configured to receive the fibrous substrate therein and store the fibrous substrate at a temperature at or below −80° C. The container may be filled at least in part with liquid nitrogen.

In a further aspect of the present invention, a method for cryopreservation of tumor cell spheroids may be provided. The method comprises obtaining a suspension of isolated tumor cells in a cell culture medium comprising a cryoprotectant. In particular, the tumor cells may be selected from a group consisting of human cervical cancer cells, human breast cancer cells, human prostate cancer cells, and human seminoma cells. In certain embodiments, the suspension may comprise isolated tumor cells in a concentration from about $2\times10^3$ cell/mL to about $8\times10^3$ cell/mL. Additionally, in some embodiments, the cell culture medium may be substantially free of a hydrogel. The method may also comprise applying the suspension to a fibrous substrate comprising a network of interconnected cellulosic fibers defining a plurality of pores therein by allowing the suspension to absorb into the fibrous substrate such that the isolated tumor cells penetrate and settle to an interior of the fibrous substrate. In some embodiments, an average diameter of the plurality of pores may be from about 100 μm to about 150 μm. Moreover, an array of circular patterns of a hydrophilic agent may be coated onto the fibrous substrate. The circular patterns have diameters from about 500 μm to about 1500 μm. In addition, a hydrophobic agent may be coated onto a remainder of the fibrous substrate not coated by the hydrophilic agent. The method further culturing the tumor cells within the fibrous substrate until formation of the tumor cell spheroids. Lastly, the method includes cooling the fibrous substrate and the tumor cell spheroids formed therein to or below a temperature of −80° C.

These and other aspects of the invention will become apparent to those skilled in the art after a reading of the following detailed description of the invention, including the figures and appended claims.

BRIEF DESCRIPTION OF THE FIGURES

FIG. 3c shows another example of the cell release device of FIG. 3a.

FIG. 6 shows images of HeLa cells, incubated over 24 hr and 48 hr periods, after being retrieved from being frozen via a conventional method (left) as compared to on a paper substrate (right) for 1 month and then released from the paper after thawing and cultured with medium according to Example I.

DETAILED DESCRIPTION

Figure 1:
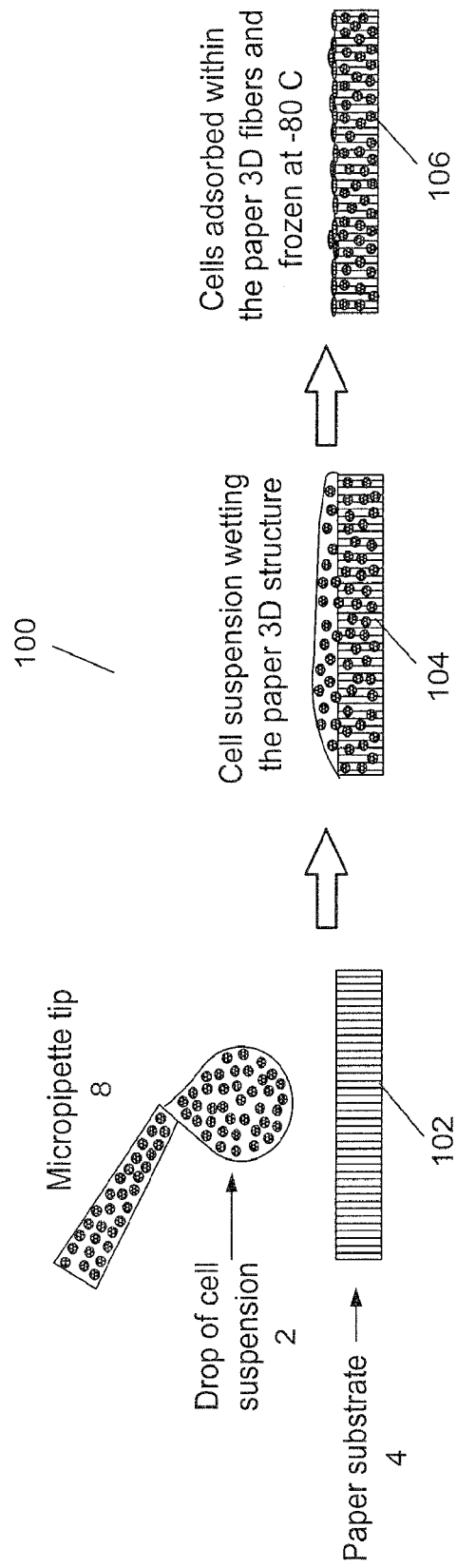
FIG. 1 shows an exemplary method cryopreservation of isolated mammalian cells within a fibrous substrate.

The present invention relates to improved systems and methods for cryopreservation of cells and/or multi-cellular aggregates that provide a more efficient way for storage and maintenance of the cryopreserved samples that allows for easy retrieval in desired quantities while reducing contamination risks and cellular damage as compared to conventional storage methods that require repeated freezing and thawing cycles of an entire stock of cryopreserved cells every time sample is to be retrieved. Long-term preservation of cells, in particular, mammalian cells, in suspension in large containers encounters major challenges relating to space, cost of maintenance, and cross-contamination risks. The improved systems and methods of the present application provide new ways for cryopreservation/vitrification. It is believed that the improved systems and methods for cryopreservation/vitrification described herein overcome and/or reduce the above-identified challenges.

The present application describes herein improved systems and methods for cryopreservation of cells, such as, for example, mammalian cells, within paper platforms so as to overcome and/or reduce the challenges of cryopreservation of cells in suspension in large containers. More particularly, the improved systems and methods for cryopreservation may utilize a fibrous substrate, e.g., a paper-based substrate in and/or on which cells may reside and/or attached, and maintained therein for vitrification. The paper-based substrate, when in use for cell cryopreservation, may be arranged in any suitable configuration, including for example, a flat sheet, a sheet folded in any desired orientation or manner, or a continuous sheet of the paper-based substrate rolled about a longitudinal axis of a central tube. It is noted that the folded and rolled configurations may provide a more space efficient arrangement that further allows for space savings and therefore, more efficient cryopreservation and maintenance of frozen cells. In addition to providing a more space efficient substrate for storage, the paper-based substrate, which has a three-dimensional porous structure, may also provide a three-dimensional porous network of fibers that is believed to support cell integrity during freezing. More particularly, it is believed that penetration of cells into the three-dimensional porous network of fibers of a paper-based substrate may provide for scaffolding for cells to attach and/or an external structure for protecting cell integrity and/or cell viability during the vitrification process. Although the exemplary embodiments described herein refer to a paper-based substrate, it is contemplated that the systems and methods for cryopreservation of cells described herein may be applied to other suitable fibrous substrates, such as, for example, scaffolds, textiles, yarn fibers and networks, threads and fabrics, cotton fibers and mats, nylon meshes, natural and glass wool, etc.

For example, the cells may be suspended in cell culture media along with one or more cryoprotective agents, and may then be absorbed by a fibrous material, such as, a piece of paper. Cells can penetrate inside paper with large pore size (e.g., up to 50 μm or up to 100 μm) and settle in the 3D fibrous environment. The present application provides the use of fibrous substrates, in particular, paper substrates, for cell cryopreservation procedures, where porous paper substrates offer 3D structural support for cells and/or multi-cellular aggregates formed therein during freezing, facilitate storage, sampling, and shipping to customers. Furthermore, it is contemplated that the present invention may be applicable to large scale cryopreservation of cells using rolls of papers. Storage of rolled paper substrates can be achieved in large containers in liquid nitrogen, and taking out small samples for customers could be achieved by cutting a small piece of the paper roll to be shipped without thawing the entire roll.

Cryopreserved cells using the systems and methods of the present application may be released using a thawing device that is described further herein. Alternatively, cells can be left within the paper after thawing, which permits 3D cell culture and/or 3D spheroid models within the paper. In some embodiments, some portion of cells may remain within the paper even after release steps, which can also be utilized for 3D cell culture and/or 3D spheroid models.

In a first aspect of the present application, a system and method for cryopreservation of isolated cells is provided. The isolated cells may be suspended in any suitable medium for application onto a paper substrate and subsequent cryopreservation. The isolated cells may comprise any type of cells suitable for vitrification, including eukaryotes or prokaryotes. For example, the isolated cell may include, for example, isolated mammalian cells. In one aspect, the isolated mammalian cells may include cells from any suitable mammal, such as, for example, rodent (e.g., mice or hamster), pig, monkey. The isolated mammalian cells may be primary cells, a finite or an immortal cell line. In particular, the isolated mammalian cells may comprise cells of human origin, which may also be either a finite or an immortal cell line. In another aspect, the isolated mammalian cells may include adherent or non-adherent cell types, and may include, for example, cervical cells, epithelial cells, prostate cells, testicular cells, germ cells, tumor cells, blood cells, haploid cells, etc. In particular, the isolated mammalian cells may comprise, for example, human cervical cancer cells, human breast cancer cells, human prostate cancer cells, human seminoma cells, etc. More particularly, the isolated cells may comprise, for example, HeLa cells, MCF-7 cells, PC-3 cells, JKT cells, A549 cells, MDA-MB-231 cells, THP-1 cells, LNCaP cells, DU145 cells etc.

The isolated cells may be suspended in any suitable medium for maintaining viability of cells in a vitrification process. For example, the isolated cells may be suspended in any suitable cell cryopreservation media, such as, for example, Cell Freezing Medium commercially available from Sigma Aldrich, USA. In one embodiment, the cell cryopreservation media may comprise cell culture media in combination with at least one cryoprotective agent. The cell culture media may comprise any suitable media for supporting culturing and growth of the isolated cells, in particular, isolated mammalian cell, more particularly, isolated human cell, and even more particularly isolated human tumor cells. The cell culture media may comprise an aqueous media having various addition components such as amino acids, sugars, serum, etc. In certain embodiments, the cell culture media may comprise serum. For example, the cell culture media may comprise a Minimum Essential Medium optionally in combination with calf serum and/or fetal bovine serum. In another example, the cell culture media may comprise Dulbecco's Modified Eagle's medium. In other embodiments, the cell culture media may be serum free. Additionally, any suitable cryoprotective agent that preserves cell integrity and/or cell viability for freezing and subsequent thawing of cells may be used. For example, the cryoprotective agent may comprise glycerol, dimethyl sulfoxide (DMSO), or a combination thereof.

In one exemplary embodiment, a filter paper platform may be used for freezing cells in a 3D environment, and may provide structural support to the cells that protect cell integrity during freezing. FIG. 1 shows an exemplary cell freezing protocol for a method for paper-based mammalian cell cryopreservation within paper platforms. In certain embodiments, the paper substrate may be stored at a freezing temperature (e.g., at −80° C. or below). When a sample of the cells need to be retrieved, the paper substrate may be cut to any desired size and shape and allowed to thaw by raising the temperature of the paper substrate. The paper may then be washed several times to release cells from the substrate. The resulting suspension may then be centrifuged and the cells may be recovered thereafter.

As shown in FIG. 1, an exemplary method 100 for cryopreservation of isolated mammalian cells is shown. A suspension of isolated mammalian cell 2, in particular, isolated mammalian cell, more particularly, isolated human cell, and even more particularly isolated human tumor cells in a cell cryopreservation medium may be prepared. The cell cryopreservation medium may include any suitable amounts of one or more cryoprotective agents. For example, the medium may comprise from about 1 to about 15 percent (g/mL) of one or more cryoprotective agents, or from about 5 to about 10 percent (g/mL) of one or more cryoprotective agents. The suspension of isolated mammalian cells 2 may be applied to a fibrous substrate 4 using any suitable tools. For example, on a small scale, the suspension of isolated mammalian cells 2 may be applied via a micropipette having a micropipette tip 8 for delivering the suspension to the substrate 4. As shown in step 102, the suspension of isolated mammalian cells 2 may be applied via a micropipette tip 8 to the fibrous substrate 4. The suspension of isolated mammalian cells 2 may be allowed to rest on the fibrous substrate 4 for a predetermined period of time to allow the cell suspension to wet and penetrate the fibrous substrate 4, as shown in step 104. The combination of the cell suspension 2 and the fibrous substrate 4 may be allowed to further rest to permit the cells to adsorb to further penetrate and adsorb to the fibrous substrate 4, as shown in step 106. After the cells are permitted to adsorb to the fibrous substrate 4, in some embodiments, the cells may then penetrate through the entire thickness of the fibrous substrate 4. In certain embodiments, the cells penetrate through the entire thickness of the fibrous substrate 4 and be homogeneously distributed throughout. The cells adsorbed within the structure of the fibrous substrate 4 may then by cryopreserved by cooling the combination of the cell suspension 2 and the fibrous substrate 4 to a temperature at or below −80° C. In one exemplary embodiment, the combination of the cell suspension 2 and the fibrous substrate 4 may be cooled by applying liquid nitrogen.

The fibrous substrate 4 may comprise a network of interconnected cellulosic fibers defining a plurality of pores therein. In one particular embodiment, the fibrous substrate 4 may comprise any suitable forms of a fibrous material for cell seeding and cryopreservation, such as, for example, paper (e.g., cellulose filter paper). An average size of the pores of the fibrous substrate 4 may be any suitable average size to allow penetration into and adhesion of mammalian cells within the substrate 4. For example, an average diameter of the plurality of pores of the substrate 4 may be from about 20 μm to about 200 μm, or from about 50 μm to about 150 μm. In certain embodiments, the average size of the pores less than or equal to about 100 μm, or less than or equal to about 50 μm. The fibrous substrate 4 may have any suitable thickness for cell adhesion and cryopreservation, such as, for example, from about 50 μm to about 300 μm, from about 100 μm to about 250 μm, or from about 150 μm to about 200 μm.

Additionally, the fibrous substrate 4 may be untreated or may be treated with one or more additives. For example, the additives may promote structural strength of the fibrous substrate 4, adhesion of the isolated mammalian cells to the substrate 4 and/or enhance viability of the cells through a freeze-thaw cycle. In one particular embodiment, the fibrous substrate 4 may be treated with a coating that improves the structural strength of the substrate 4, such as, for example, a chemically stable resin that is suitable for use with cryopreservation and cell culture. For example, the chemically stable resin may include, for example, epoxy resins, acrylamide copolymers, strengthening agent Polystron, polyacrylamide resins, paraffin wax, polyamide-polyamine derivatives resin, Stylenic resins, Acrylic resins, Olefin resins, etc. The fibrous substrate 4 may also include any suitable additive that promotes cellular adhesion and/or cellular viability through a vitrification process, such as, for example, one or more components typically found in extracellular matrix (e.g., one or more extracellular matrix agents, glycoproteins, monobody, substrate adhesion molecules, mucins, collagen, laminin, elastin, etc.). Specifically, the fibrous substrate 4 may be coated with fibronectin.

Furthermore, the additives may include hydrophilic and/or hydrophobic agents. For example, a hydrophilic agent may comprise fibronectin, extracellular matrix agents, substrate adhesion molecules, laminin, or hydrogels. Alternatively, the substrate may include bare unmodified regions that may have hydrophilic properties. The hydrophobic agent may include nanoparticles such as nanobeads, nanorods, nanostars, nanohexapods, nanotubes, or graphene, or may comprise silane compositions, such as, for example, trichloro (1H,1H,2H,2H-perfluorooctyl) silane (PFOTS)), aminosilanes, glycidoxysilanes, mercaptosilanes, or perfluorodecyltrichlorosilane (FDTS), etc. The hydrophilic and/or hydrophobic agents may each coat or be deposited (e.g., via vapor deposition, nanoimprint lithography, or capillary printing, etc,) on a selected surface region on the fibrous substrate 4. In some embodiments, the fibrous substrate 4 may be coated with both hydrophilic and hydrophobic agents. In particular, the hydrophilic agent covers certain regions on the fibrous substrate 4 and the hydrophobic agent covers other regions on the fibrous substrate 4 that are not covered by the hydrophilic agent. More particularly, the hydrophilic agents may selectively cover regions on the fibrous substrate 4 forming in a grid pattern similar to that of multi-well cell culture plates, and the hydrophobic agents may cover the remainder of the fibrous substrate 4, thereby forming hydrophilic "wells" on the surface of the fibrous substrate 4 for cell adhesion. In one particular example, each of the "wells" may comprise a hydrophilic coating in a circulate shape, wherein the diameter of the circle may be from about 500 µm to about 1500 µm.

Although the exemplary embodiment shown in FIG. 1 provides a small scale method for cryopreservation of isolated mammalian cells, it is also contemplated that the suspension of isolated mammalian cells 2 may be applied to a fibrous substrate 4 on a larger commercial scale and subsequently cryopreserved by reducing cooling the commercial scale combination of the cell suspension 2 and the fibrous substrate 4 to a temperature at or below −80° C. This method may be applied to sheets of papers (e.g., paper sizes from 4A0 to A10) and may be automated utilizing inkjet printing technology for preparing substrates by coating, patterning, and applying cell suspensions, and followed by cryopreservation and storage. The technology may also be applied to rolls of paper (e.g., 11, 17, 18, 22, 24, 30, 34, 36, or 42 inches wide rolls) where a system may be developed for automated paper roll handling for preparation of paper including un-rolling, coating and patterning, application of cell suspensions, followed by re-rolling, automated cryopreservation and storage. For example, the fibrous substrate 4 may be in the form of a long continuous sheet that is a rolled about a longitudinal axis of a central tube, and the suspension of isolated mammalian cells 2 may be applied to the entire roll of the fibrous substrate 4 by wetting the entire roll with the suspension. The suspension may then be allowed to penetrate the roll, and the cells may be adsorb to the fibrous substrate 4 throughout the roll. In some embodiments, the suspension of isolated mammalian cells 2 may saturate the entire roll of the fibrous substrate 4.

It is believed that certain embodiments of the improved systems and methods for cryopreservation of isolated mammalian cells as described above may provide a high percentage of cell viability after cryopreservation. For example, the cells may be at least 60%, at least 70%, at least 80%, or at least 90% viable after cryopreservation and subsequent thawing from the paper substrate. In certain embodiments, it is believed that a paper-based substrate coated with fibronectin may provide comparable or improved cell viability as compared to conventional cryopreservation, which suspends the cells in medium and freezing said suspension in small vials.

In some embodiments, using the previously described paper substrates, this paper-based cell cryopreservation technique be limited in its efficiency of cell release. Since cells penetrate within the paper 3D porous structure before freezing (see FIG. 1) they are challenging to get released after thawing and washing the paper. It appears that the cells may be mechanically trapped within the paper substrate. To solve this challenge, two different approaches may be utilized: (1) modifying the concentration of cells applied to the fibrous substrate before freezing by cryopreservation; and (2) creating a gentle release method and device that avoids excessive and harmful washings of the cells. Although a suspension having any suitable concentration of cells may be applied to the paper substrate, it is believed that a higher concentration of cells may improve cell release and/or viability. It is believed that a high concentration of cells is recommended because of the thickness of the paper substrate, where more cells need to occupy the gaps therein and be close to each other. A suspension having any suitable concentration of cells may be applied to the paper substrate. For example, cells may be cultured at different concentrations on a paper substrate of 50 mm in diameter, e.g., starting from $10^6$ cells and up to $10^7$ cells on each 50 mm paper substrate. In this example, it is believed that a cell concentration of $10^7$ may be optimal. In another example, the suspension may include isolated mammalian cells suspended in the cell cryopreservation medium at a concentration from about $10^4$ to about $10^9$ cells/mL, from about $10^4$ to about $10^6$ from about $10^6$ to about $10^8$ cells/mL, from about $10^6$ to about $10^7$ cells/mL, or about $10^7$ cells/mL.

The second approach as discussed above provides for a gentle release method and a new device that reduces excessive washing steps for releasing the cells from the fibrous substrate. The concept of the device is based on an observation that leaving the thawed paper substrate in culture can release more cells in addition to the cells that had already been released by physical agitation using washing steps. For example, the device may comprise a porous hydrophilic membrane/mesh (e.g., pore size 20-40 µm, or 30 µm or less) which lay between the cell culture media and the cells-on-paper assembled in cell culture plate, so the cells can be released from the paper overnight, or preferably within a few hours, pass through the pores of the membrane, reach and attach to the substrate.

Figure 2:
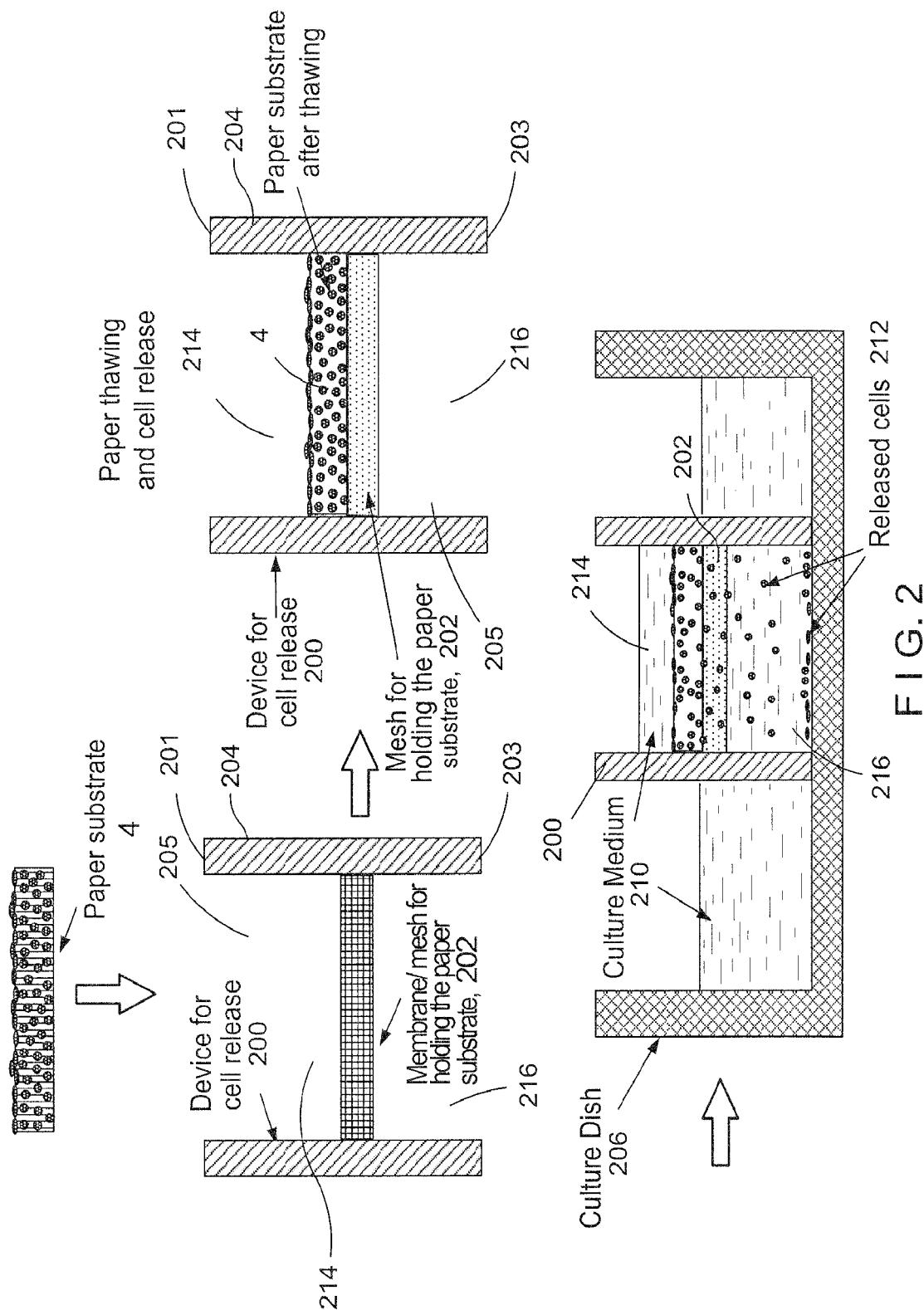
FIG. 2 shows an exemplary embodiment of an apparatus for cell release.

FIG. 2 shows an exemplary embodiment of an apparatus for cell release. The device may allow gentle cell release without additional mechanical forces, such as turbulence from repeat washings, to the paper substrate. Furthermore, the released cells obtained using the device may be spread and grow all over a predetermined surface area (e.g., cell culture plate) so as to provide a more even distribution of the released cells and avoid accumulation of cells in any particular area. As shown in FIG. 2, an exemplary embodiment of a gentle release device 200 may comprise a first tubular structure 204 having a first lumen 205 extending longitudinally from a first end 201 to a second end 203. The first tubular structure 204 may have a circular or a substantial circular cross-sectional shape. However, it is also contemplated that the first tubular structure 204 may have any suitable shape for receiving a sample of cells preserved on a fibrous substrate 4, such as, for example, oval, square, rectangular, or any other regular or irregular shape.

The device 200 may also include a mesh or a membrane 202 positioned within the first lumen 205 and transverse to the longitudinal axis of the first tubular structure 204. The mesh or membrane 202 may be permanently affixed within the first lumen 205 by any suitable means, such as, for example an adhesive 219 (e.g., Norland optical adhesives (NOAs)). The mesh or membrane 202 in combination with internal walls of the first tubular structure 204 define an upper cavity 214 for receiving a sample of cells cryopreserved on a fibrous substrate 4 therein. The remainder of the first lumen 205, which is below the mesh or membrane 202 and enclosed by the internal walls of the first tubular structure 204, defines a lower cavity 216. In one embodiment, the mesh or membrane 202 may be positioned substantially along a midpoint of a length of the first tubular structure 204 such that the upper cavity 214 is substantially the same size as the lower cavity. In another embodiment, the upper cavity 214 may be larger than the lower cavity 216. In an alternative embodiment, the upper cavity 214 may be smaller than the lower cavity 216. The mesh or membrane 4 provide a porous barrier for holding the fibrous substrate 4, while allowing cells to penetrate therethrough and move from the upper cavity 214 to the lower cavity 216. The mesh or membrane 202 may comprise any suitable porous barrier that selectively permits passage of cells therethrough while holding the fibrous substrate. The mesh or membrane 202 may have any suitable pore size for permitting the cells to pass therethrough. For example, the mesh or membrane 202 may have a pore size from about from about 10 µm to about 50 µm, from about 20 µm to about 40 µm, or about 30 µm.

As can be seen in FIG. 2, when in use, a sample of cells cryopreserved on a fibrous substrate 4 may be placed into the upper cavity 214 on top of the mesh or membrane 202. The sample may be frozen or thawed. If the sample is frozen, it may be allowed to rest on the mesh or membrane 202 for a predetermined period of time to allow the sample to thaw. In some embodiments, the sample is rested on the mesh or membrane 202 until it warms to room temperature before any washing steps. When in use, the device 200 may be placed within an external plate 206, such as cell culturing plate (e.g., a Petri Dish). The second end 203 of the device may touch an interior surface of a base of the culturing dish 206. The external plate 206 may be partially filled with a culture medium 210 so that the second end 203 of the device 200 is submerged within the culture medium 210. In certain embodiments, the external plate 206 may contain sufficient amounts of culture medium 210 such that the lower cavity is completely filled by culture medium 210. The sample of cells cryopreserved on the fibrous substrate 4 may be loosened from its substrate 4 by mechanically agitating the device 200 within the external plate 206. The cells may also be loosened from the fibrous substrate 4 by one or more washing steps using any suitable fluid, in particular, the culture medium 210. For example, fluid, such as the culture medium 210 may be applied to the upper cavity 214 so as to wash through the substrate 4. In some embodiments, the fluid may be applied in a turbulent manner to increase mechanical agitation to the substrate 4. This washing process may be repeated for as many times as desired to release cells from the substrate 4, through the mesh or membrane 202 and collect the cells within the lower cavity 216. The released cells 212 may be released into the cell culture medium 210 filling the lower cavity 216. In some embodiments, the released cells 212 may be suspended in the culture medium 210 filling the lower cavity 216.

Figure 3A:
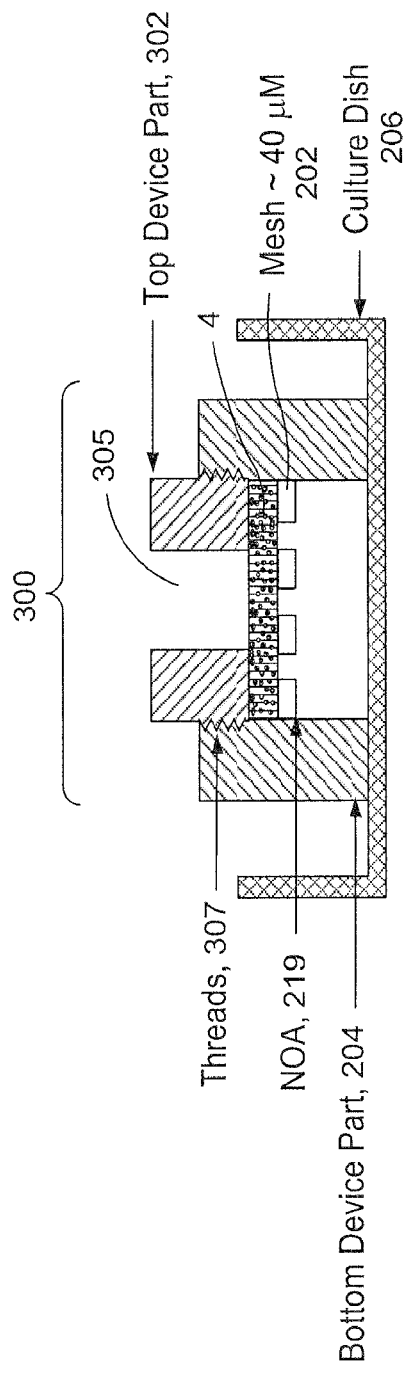
FIG. 3a shows an alternative exemplary embodiment of a cell release device when it is in use with a sample placed therein.
Figure 3B:
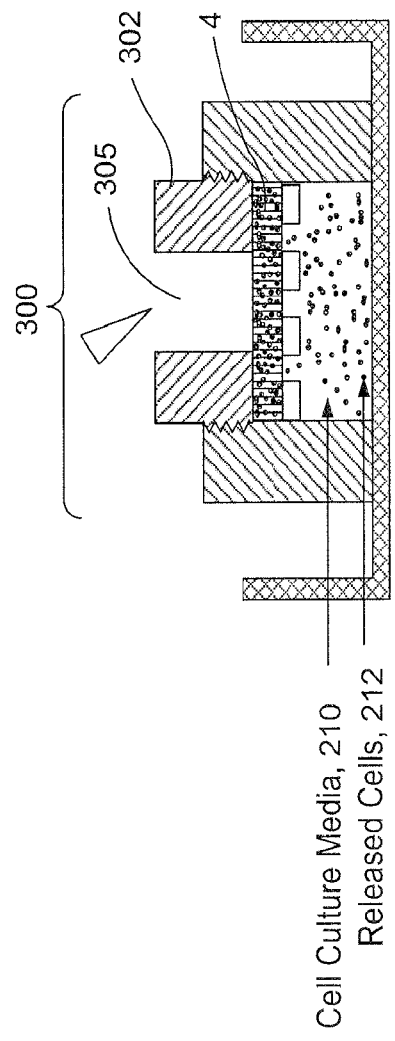
FIG. 3b shows the exemplary embodiment of a cell release device of FIG. 3a when it is in use for release of cells from a fibrous substrate.
Figure 3C:
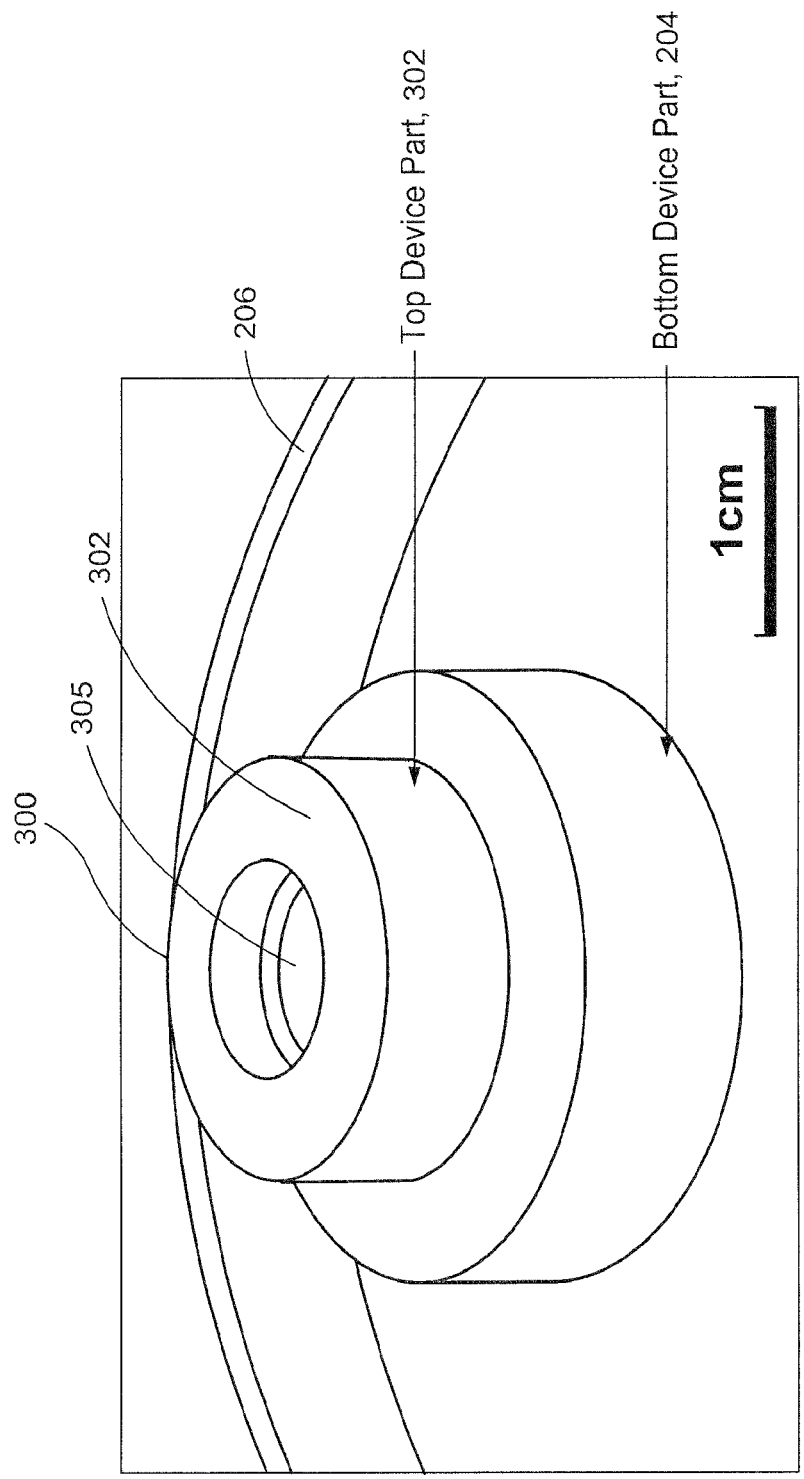

Another exemplary device for releasing cells after thawing is shown in FIGS. 3a to 3c. The device may be manufactured using 3D printing. In particular, the exemplary device of FIGS. 3a to 3c may provide high release and viability efficiencies. In certain embodiments for paper-based 3D culture, the platform can be thawed without releasing the cells, where cells can grow and form aggregates. FIGS. 3a and 3b provide schematics of a thawing device that releases cells to a cell culture plate (e.g., regular Petri Dish). FIG. 3c provides a drawing of the 3D printed cell release thawing device.

The exemplary device 300 shown in FIGS. 3a to 3c is substantially similar to the device 200 described above with respect to FIG. 2, except as further noted below. However, this alternative embodiment of a device 300 for releasing cells from a fibrous substrate includes a bottom portion, which corresponds to the first tubular structure 204 as described above, and further includes a top portion 302 that is configured to be inserted, at least in part, into the first lumen 205 of the first tubular structure 204. The top portion 302 may comprise a second tubular member extending along a second longitudinal axis. The second tubular member may have a cross-sectional shape that substantially corresponds to a cross-sectional shape of the first lumen 205. In particular, the second tubular member may have an outer cross-sectional circumference that substantially conforms to the cross-sectional size and shape of the interior wall of the first lumen 205 so as to provide a matching fit. The second tubular member may also have a second lumen 305 extending along the second longitudinal axis. In certain embodiments, as shown in FIG. 3c, both the first and second tubular members may have circular cross-sectional shapes. In particular, the first and second tubular member may be coaxially aligned.

When in use, the top portion 302 may be inserted into the upper cavity 214 of the first tubular member 204 on top of the sample of cells cryopreserved on a fibrous substrate 4. The top portion 302 may physically press the fibrous substrate 4 against the mesh or membrane 4 so as to hold the substrate 4 while mechanically agitating the device 300 within the external plate 206 and/or washing of the substrate 4. The top portion 302 may be held in place by the weight of the top portion 302 itself. Alternatively, as shown in FIG. 3a, at least a portion of an exterior surface of the top portion 302 may be comprise threading 307 configured to engage matching threading within an interior surface of the first lumen 205 so that the top portion 302 may be reversibly threaded towards and away from the fibrous substrate 4 or mesh or membrane 4. The top portion 302 may be threadedly advanced towards to control an amount of pressure applied against the fibrous substrate 4, or mesh or membrane 4.

In this alternative embodiment of a cell release device 300, the cells may also be further loosened from the fibrous substrate 4 by one or more washing steps using any suitable fluid, in particular, the culture medium 210, delivered to the substrate 4 via the second lumen 305. For example, fluid, such as the culture medium 210 may be applied to the second lumen 305 so as to wash through the substrate 4. In some embodiments, the fluid may be applied in a turbulent manner to increase mechanical agitation via the second lumen 305 to the substrate 4. This washing process may be repeated for as many times as desired. The released cells 212 may be released into the cell culture medium 210 within the lower cavity 216.

In another aspect of the present application, a system and method for cryopreservation of a cell culture, in particular, multi-cellular aggregates, more particularly, tumor spheroids, may be provided. In one example, any of the isolated cells, in particular, any of the isolated mammalian cells, as discussed above, may be suspended in a hydrogel medium, applied to a fibrous substrate 4, to form a fibrous three-dimensional cell culture substrate. The hydrogel medium may be formed from any suitable cell culture medium and a hydrogel component. The hydrogel component may comprise any comprise any suitable hydrogel, for example, extracellular matrix hydrogel. In one specific example, the hydrogel medium may be Matrigel, commercially available from Corning Life Sciences and BD Biosciences. The fibrous three-dimensional cell culture substrate, along with the cells applied thereto, may be directly cryopreserved or may be cultured for a predetermined period of time prior to cryopreservation. For example, the fibrous three-dimensional cell culture substrate along with the cells from the suspension may be cultured for a period of 2 or 3 days, 1 week, 2 weeks, 3 weeks or a month. In one particular example, the cells may be cultured for 2 weeks. In another example, the cells may be cultured for a period of time sufficient to obtain uniform three-dimensional distribution of cells within the substrate. After the cells have been cultured, a cryopreservation may be added to the fibrous three-dimensional cell culture substrate and the cultured substrate may be subsequently cryopreserved. In a similar as manner as discussed above, the fibrous three-dimensional cell culture substrate may be cryopreserved by cooling the substrate to a temperature at or below −80° C., such as by applying liquid nitrogen.

In one example, a system and method for cryopreservation of 3D cultures of cells, in particular mammalian cells suspended in hydrogel solution and loaded to the 3D fibrous platform, and cultured for few weeks to form 3D culture may be provided. For example, cells may be suspended in Matrigel solution, loaded to the paper platform, and then left to grow in culture for 2 weeks, or more, for forming a 3D culture. After the 3D culture is formed, cryopreservation agents may be added to the system, get adsorbed by the fibrous platform, and followed by storing at a freezing temperature (e.g., at −80° C. or below). The present invention provides the use of paper substrates for 3D cell culture cryopreservation procedures, where porous paper substrates offer 3D structural support for the culture during freezing, facilitate storage, sampling, and shipping to customers. Furthermore, it is contemplated that the present invention may be applicable to large-scale cryopreservation of 3D cells cultures using rolls of papers. Storage of rolled paper substrates can be achieved in large containers in liquid nitrogen, and taking out small samples for customers could be achieved by cutting a small piece of the paper roll to be shipped without thawing the entire roll.

In another example, a system and method for cryopreservation of cultured multi-cellular aggregate, in particular, tumor spheroids, may be provided. Isolated tumor cells may be suspended in any suitable cell culture medium, as discussed above, for application onto a fiberous substrate, subsequent cell culturing to form tumor spheroids on or within the substrate, and cryopreservation. In particular, the cell culture medium may be an aqueous medium. In some embodiments, the cell culture medium may include a hydrogel, while in other embodiments the cell culture medium may be free of any hydrogel components. More particularly, the cell culture medium may be without any hydrogel components for forming a three dimensional cell culture substrate (e.g., without Matrigel). The isolated tumor cells may comprise human tumor cells. In particular, the isolated tumor cells may comprise, for example, human cervical cancer cells, human breast cancer cells, human prostate cancer cells, human seminoma cells, etc. More particularly, the isolated tumor cells may comprise, for example, HeLa cells, MCF-7 cells, PC-3 cells, MDA-MB-231 cells, HCT116 cells, A549 cells, etc. Even more particular, the isolated tumor cells may comprise, HeLa cells and/or MCF-7 cells.

The fibrous substrate may comprise a network of interconnected cellulosic fibers defining a plurality of pores therein. In one particular embodiment, the fibrous substrate may comprise any suitable forms of a fibrous material for cell seeding and cryopreservation, such as, for example, paper (e.g., cellulose filter paper). In addition, the paper may be coated with both a hydrophilic agent (e.g., fibronectin) and a hydrophobic (e.g., silane compositions, such as, tri chloro (1H,1H,2H,2H-perfluorooctyl) silane (PFOTS)). The hydrophilic and/or hydrophobic agents may each coat or be deposited (e.g., via vapor deposition) on a selected surface region on the fibrous substrate 4. In particular, the hydrophilic agent covers certain regions on the fibrous substrate 4 and the hydrophobic agent covers other regions on the fibrous substrate 4 that are not covered by the hydrophilic agent. More particularly, the hydrophilic agents may selectively cover regions on the fibrous substrate 4 forming in a grid pattern similar to that of multi-well cell culture plates, and the hydrophobic agents may cover the remainder of the fibrous substrate 4, thereby forming hydrophilic "wells" on the surface of the fibrous substrate 4 for cell adhesion. In one particular example, each of the "wells" may comprise a hydrophilic coating in a circulate shape, wherein the diameter of the circle may be from about 500 µm to about 1500 µm. It is believed that these hydrophilic "wells" encourage the cells to localize and aggregate therein, and thereby, promote formation of tumor spheroids within these hydrophilic "wells."

The fibrous substrate may be cultured for a predetermined period of time so as to form tumor spheroids therein prior to cryopreservation. The substrates may be cultured for a period of 2 or 3 days, 1 week, 2 weeks, 3 weeks or a month. In one particular example, the cells may be cultured for a period of time sufficient to allow formation of tumor spheroids within the substrate, which may be, for example from about 48 hours to about 72 hours. After spheroid formation, a cryopreservation may be added to the substrate and the cultured substrate may be subsequently cryopreserved by cooling the substrate to a temperature at or below −80° C., such as by applying liquid nitrogen.

In one particular example, a system and method for growing tumor spheroids in arrays within the 3D fibrous platform may be provided. A piece of paper may be turned hydrophobic by means of chemical vapor deposition of silane. The paper platform may then be patterned in an array of hydrophilic regions by means of selective UV exposure through a hard mask fabricated by 3D printing. The hydrophilic regions of the paper may then be coated with fibronectin, followed by loading the cells suspended in culture medium. Cells may be left in culture within the paper for few days, or weeks, to allow for spheroid formation. After spheroids formation, cryopreservation agents can be added to the platform, get adsorbed by the fibrous platform, and followed by storing at a freezing temperature (e.g., at −80° C. or below). The present invention provides the use of paper substrates for 3D cell spheroids cryopreservation procedures, where porous paper substrates offer 3D structural support for the spheroids during freezing, facilitate storage, sampling, and shipping to customers. Furthermore, it is contemplated that the present invention may be applicable to large scale cryopreservation of cell spheroid cultures using rolls of papers. Storage of rolled paper substrates can be achieved in large containers in liquid Nitrogen, and taking out small samples for customers could be achieved by cutting a small piece of the paper roll to be shipped without thawing the entire roll.

It is believed that certain concentrations of cells initially applied to the fibrous substrate may promote the cells to form tumor spheroids within the substrates in culture. In particular, it is believed that a high concentration of cells provided within the initial seeding process may promote formation of tumor spheroids during culturing of the substrates prior to cryopreservation. For example, it is believed that isolated tumor cells suspended in a cell culture medium, in particular, in a cell culture medium without any hydrogel components, may be seeded at a concentration from about $2\times10^3$ cell/mL to about $8\times10^3$ cell/mL to promote formation of tumor spheroids within the substrate during a cell culture step prior to cryopreservation.

It is also believed that certain average size of the pores of the fibrous substrate may allow for cell penetration into and adhesion of cells within the substrate, while promoting the cells to form tumor spheroids within the substrates in culture. In particular, it is believed that the an average diameter of the plurality of pores of the substrate from about 100 μm to about 150 μm may provide a three-dimension structure that promotes formation of tumor spheroids therein.

In another particular example, human tumor spheroids may be formed within a paper substrate and the subsequently cryopreserved by cooling the substrate to a freezing temperature (e.g., at −80° C. or below). This example may include a paper platform that may be patterned into a microarray of hydrophilic spots within the hydrophobic paper substrate. Hydrophilic spots may have diameters range between 500 μm to 1500 μm. The patterning may be prepared by first turning the paper hydrophobic by vaporization of trichloro (1H,1H,2H,2H-perfluorooctyl) silane (PFOTS). Next, the paper may then be patterned to form an array of hydrophilic regions by UV exposure through a 3D printed stencil. During this patterning process, the backside surface of the paper may protected with tape to keep it hydrophilic, thus enable cell culture medium penetration across the depth of the paper. The microarray of hydrophilic spots may then be coated with fibronectin at a concentration of 10 mg/mL. Cells, HeLa or MCF-7, may then suspended into culture medium at a concentration in the range of $2-8\times10^3$ cell/mL, and loaded to spots by pipetting. The paper platform may then be submerged in DMEM media and incubated at 37 degrees C. and 5% $CO_2$. Tumor spheroids may start forming with 48-72 hours and the spheroids may then be cryopreserved by storing at a freezing temperature (e.g., at −80° C. or below).

Samples of tumor spheroids may be retrieved by cutting out any number of hydrophilic "wells" or microarrays from the paper substrate and subsequently thawed for further culturing or use in screening and/or testing. For example, the tumor spheroids may be thawed and used as an in-vitro screening or testing tool for determine efficacy of cancer treatment compositions, drug testing, drug discovery, forming co-cultures, growth studies, and studies of cancer biology and its development.

EXAMPLES

Example I

Figure 4:
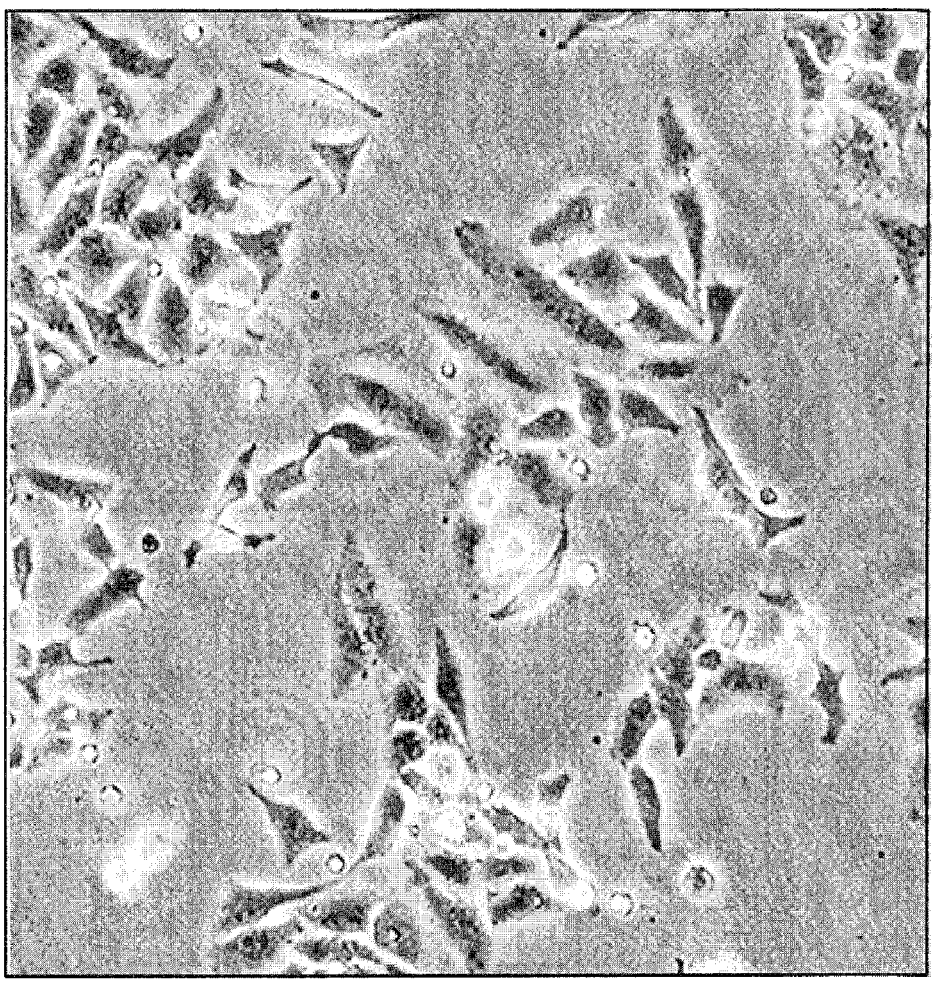
FIG. 4 shows an image of HeLa cells retrieved after being frozen on a paper substrate for 1 month and then released from the paper after thawing, and cultured with medium according to Example I.

In Example I, HeLa cells, cervical cancer cells from ATCC, suspended in Cell Freezing Medium (Sigma Aldrich, USA) was added to untreated cellulose filter paper (Whatman, UK). After that, the paper was kept inside tightly closed vial and moved to −80° C. freezer. After one month, the paper along with cells were thawed, the paper was washed several time to release cells from the paper support substrate, the suspension was centrifuged and cells were counted, and the piece of paper was cultured in cell culture flask with the appropriate medium. HeLa cells were frozen on a paper substrate for 1 month duration, and then released from the paper after thawing, and cultured with medium. FIG. 4 shows an image of retrieved cells cultured. The experiment demonstrated that cells survived the 3D-cryopreservation and cells were able to be retrieved by washing the paper (see FIG. 4).

Figure 5:
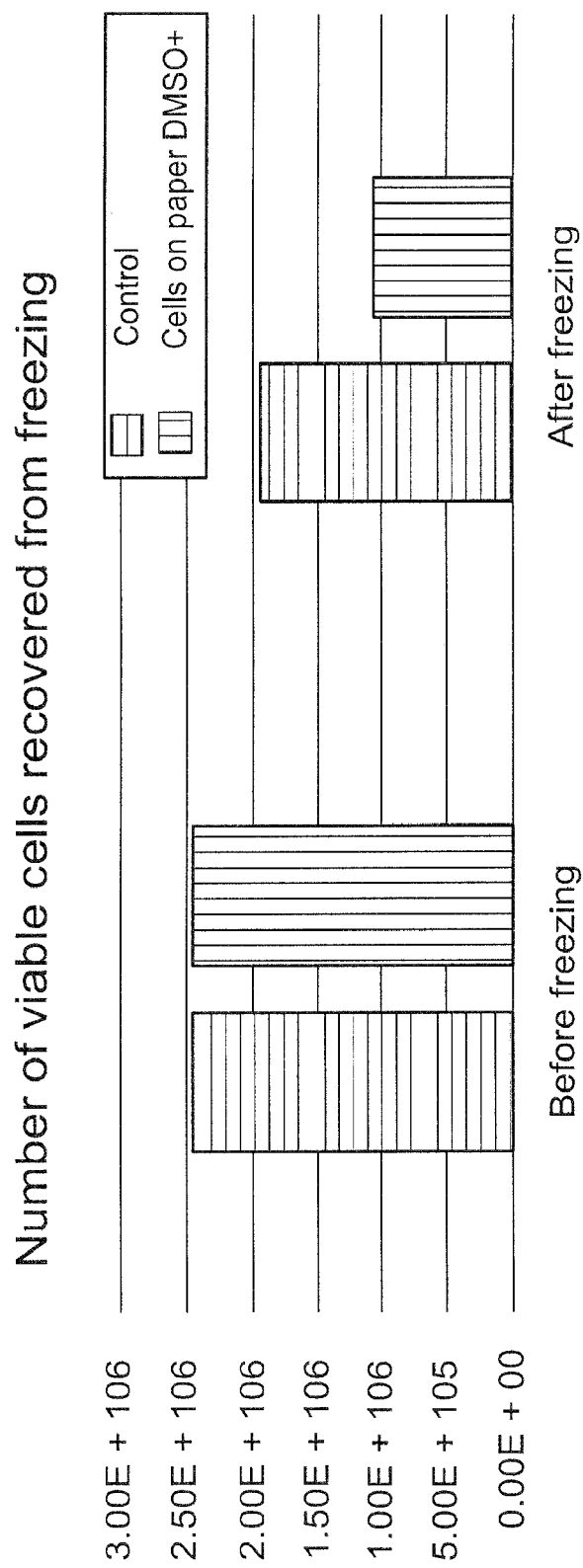
FIG. 5 shows number of retrieved viable cells counted before and after freezing on paper uncoated with fibronectin according to Example I.

FIG. 5 shows number of retrieved viable cells counted before and after freezing on paper using conventional Tryban blue staining method. The left bar of each grouping represents a control group and the right bar of each grouping represents cells cryopreserved on paper with DMSO as a cryopreserving agent. As cell retrieval was not 100% and some remained inside the paper substrate, placing the paper substrate in cell culture for few days allowed for more cell retrieval, which represent another interesting approach to retrieve cells using the proposed approach. Flow cytometry analysis demonstrated that cryopreservation-on-paper did not add any major toxicity on cells.

FIG. 6 shows images of HeLa cells, incubated over 24 hr and 48 hr periods, after being retrieved from being frozen via a conventional method (left) as compared to on a paper substrate (right) for 1 month and then released from the paper after thawing and cultured with medium. As can be seen in FIG. 6, there appears to be a similar density of cells retrieved from paper-based cryopreservation, after incubation for 24 and 48 hrs, suggesting that cryopreservation of HeLa cells may provide equivalent recovery and/or viability as compared to conventional cryopreservation methods.

After thawing the paper substrate that is containing the frozen cells, and by washing the substrate for cell release, it is noticed that the paper substrate break down into small fragments generating micro-fibers. These fibers contaminate the released cell population, and thus multiple centrifugation steps were tried to get rid of these fibers and purify released cells. However, the multiple centrifugation steps caused cell loss and lowered cell retrieval efficiency. To overcome this issue, the protocol was applied to another type of cellulose filter paper from Whatman®, 25 μm pore size and 190 μm in thickness. This paper substrate has similar properties as the previously described paper type, but with a stronger structure because it contains a chemically stable resin. The previously described experiment of Example I was repeated using the new paper substrates, and no fibers were observed the released cells.

Example II

In Example II, three different cell types, HeLa, MCF-7, and PC-3 cells were suspended in Cell Freezing Medium (Sigma Aldrich, USA) and added to cellulose filter paper coated with fibronectin (Whatman, UK). After that, each paper was kept inside tightly closed vial and moved to −80° C. freezer. After one month, the paper along with cells were thawed using the device described above and shown in FIGS. 3a to 3c.

Figure 7C:
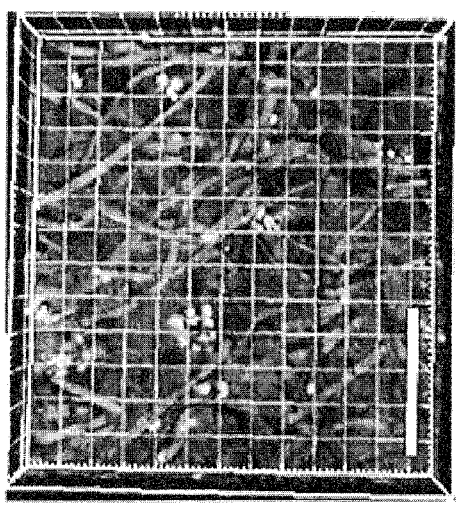
FIGS. 7a to 7c show projection of Z-stack confocal images of MCF-7 cells, cryopreserved within a paper platform, according to Example II.
Figure 7B:
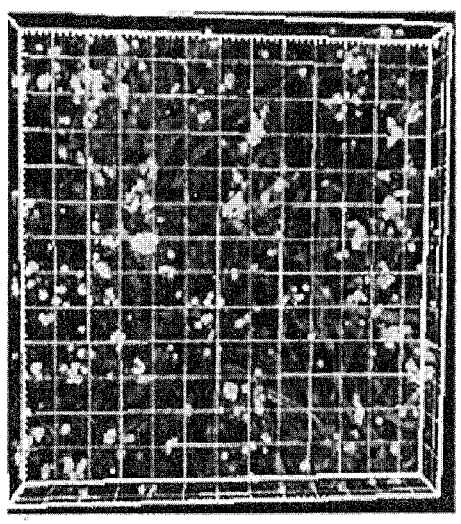
Figure 7A:

As shown in FIGS. 7a to 7b, a significant number of cells were successfully released using the developed thawing device. Specifically, FIGS. 7a to 7c show projection of Z-stack confocal images of MCF-7 cells, cryopreserved within a paper platform coated with fibronectin. FIG. 7a shows cells within the paper after thawing and before release. FIG. 7b shows around 20% of cells remained within the native paper after thawing and cell release. FIG. 7c shows less than 10% of cells remained within the fibronectin coated paper after thawing and cell release. Scale bar for FIGS. 7a to 7c is 400 μm. Interestingly, coating the paper platform with fibronectin, specific extracellular matrix glycoprotein, prior to cell loading, showed enhanced cell release (see FIG. 7c). In both cases, some cells persisted within the paper, which can be utilized for 3D cell culture even after releasing most of the cells.

Figure 8C:
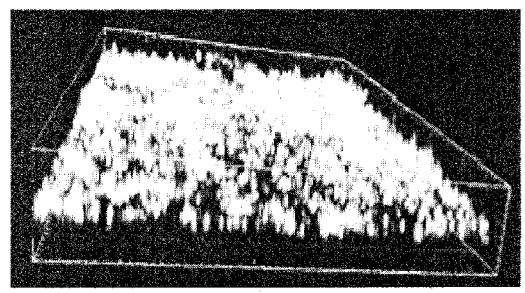
FIGS. 8a to 8c show projection of Z-stack confocal images of MCF-7 cells within paper after live/dead assay, according to Example II.
Figure 8B:
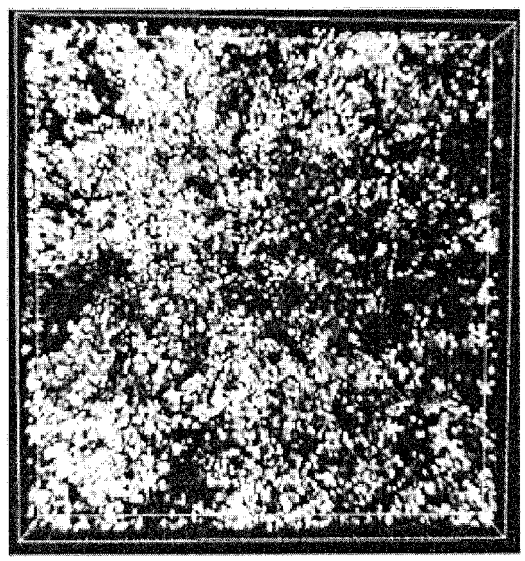
Figure 8A:
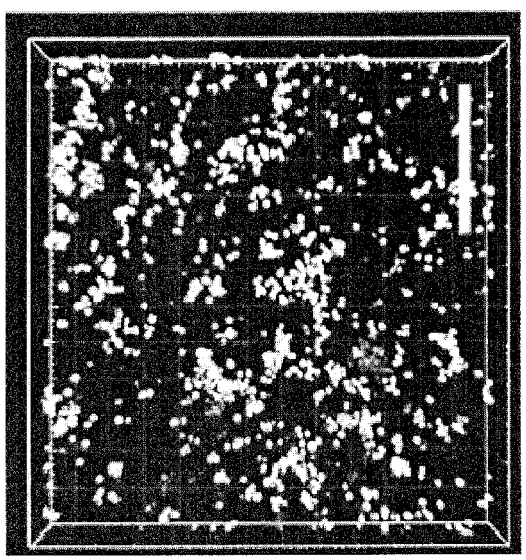

As shown in FIGS. 8a to 8c, live/dead assay within the paper coated with fibronectin revealed significant number of viable cells before freezing and after thawing. FIGS. 8a to 8c show projection of Z-stack confocal images of MCF-7 cells within paper after live/dead assay. FIG. 8a shows cells within the paper before freezing. FIG. 8b shows cells within the paper after freezing and thawing. FIG. 8c shows a side view of the Z-stack shown in FIG. 8b. Scale bar for FIGS. 8a to 8c is 400 μm.

Example III

In Example III, four different cell types, HeLa, MCF-7, PC-3 cells and JKT cells were suspended in Cell Freezing Medium (Sigma Aldrich, USA) and added to untreated cellulose filter paper, and cellulose filter paper coated with fibronectin (Whatman, UK). After that, each paper was kept inside tightly closed vial and moved to −80° C. freezer. After one month, the paper along with cells were thawed using the device described above and shown in FIGS. 3a to 3c.

Figure 9:
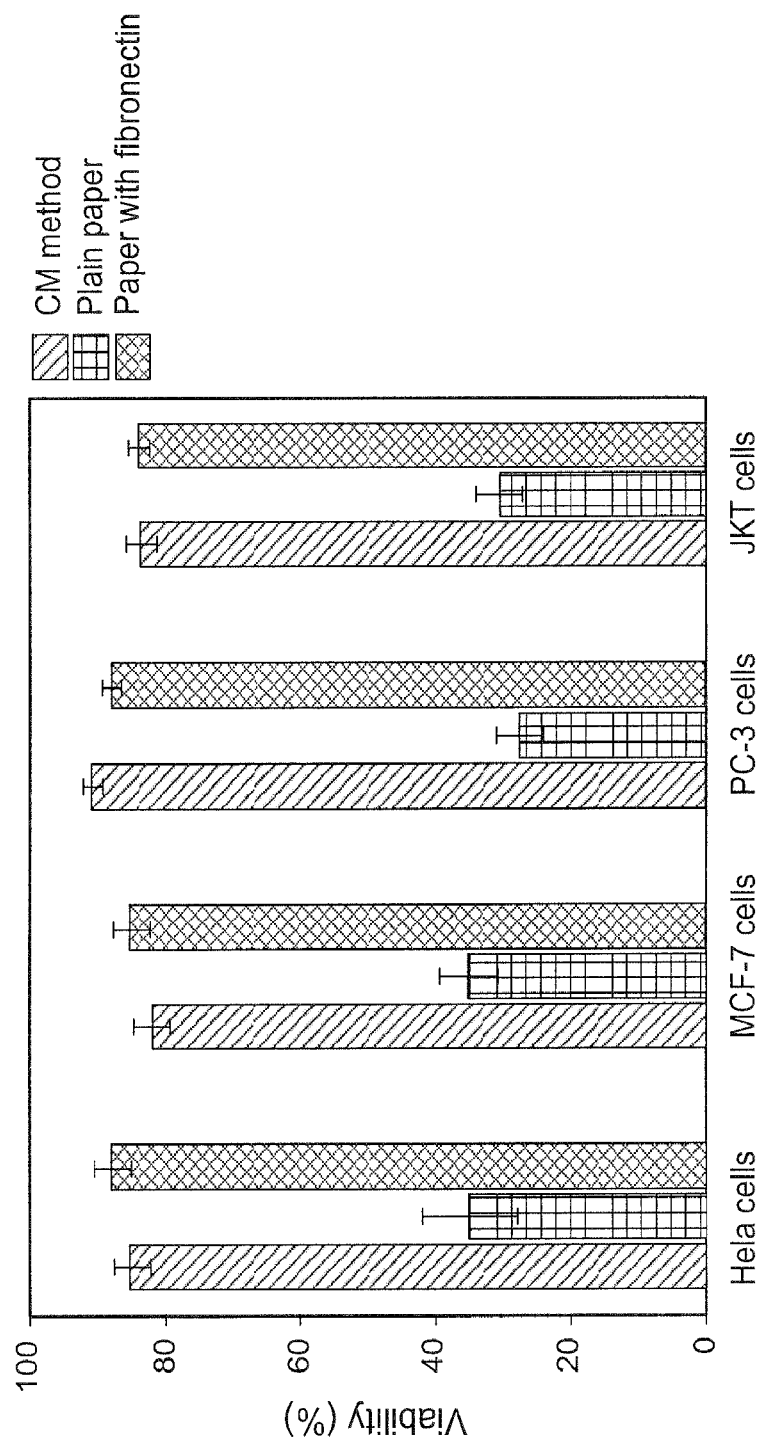
FIG. 9 shows viability results of released cells from the paper platform coated and uncoated with fibronectin after cryopreservation according to Example III.

3D cell culture was performed after thawing the different papers, without releasing the cells, to study cell functionality. FIG. 9 shows viability results of released cells from the untreated paper platform and the paper platform coated with fibronectin after cryopreservation based on Trypan Blue exclusion experiments. For each cell type, the left most bar corresponds to a conventional cryopreservation method, the middle bar corresponds to cryopreservation using untreated paper, and the right most bar corresponds to cryopreservation using paper treated with fibronectin. As can be seen in FIG. 9, the paper platform coated with fibronectin provided comparable or better viability as compared to conventional cryopreservation methods, whereas the untreated paper provided lower viability as compared to the other two methods.

Example IV

Figure 10:
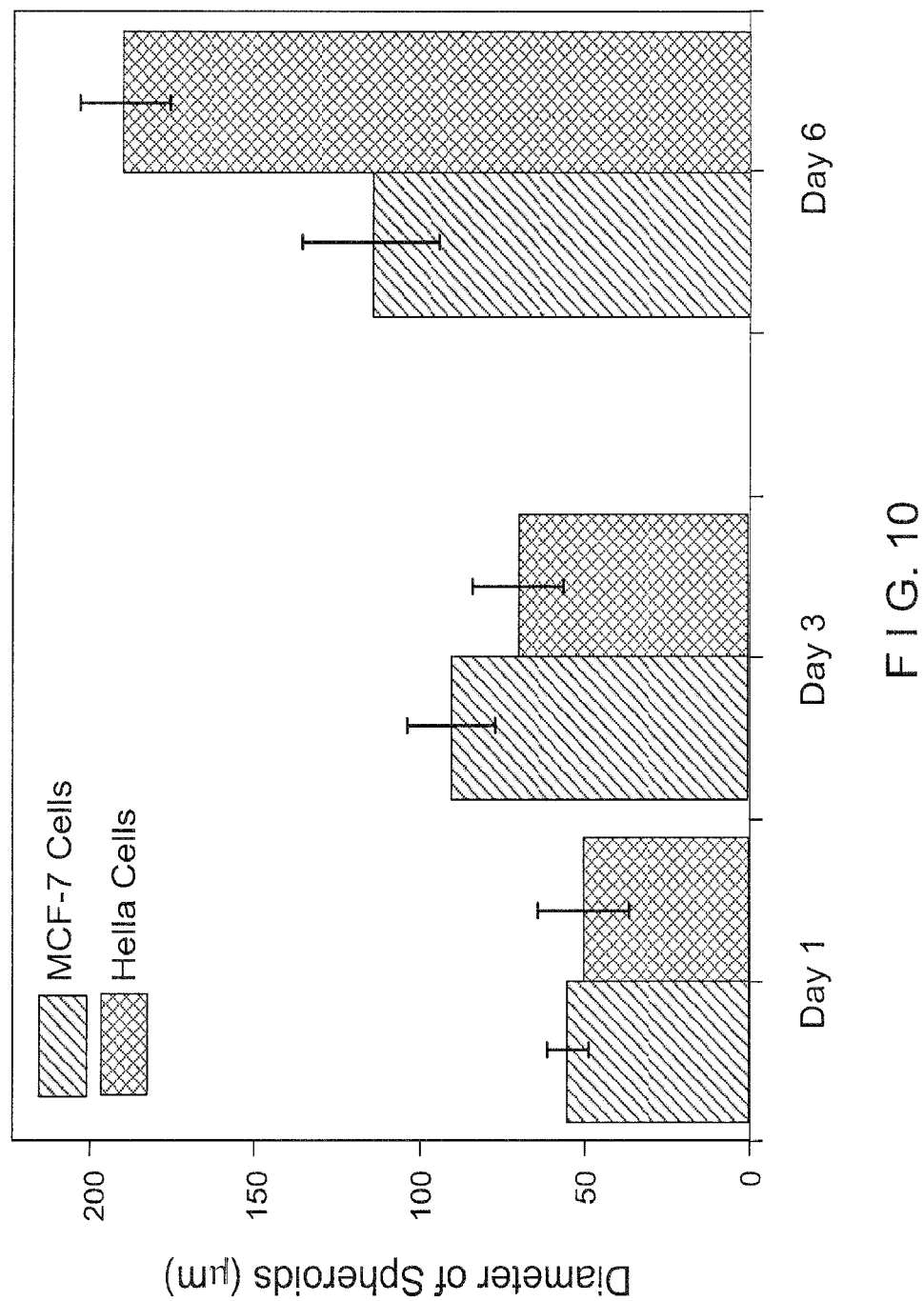
FIG. 10 shows results demonstrating an increase in diameter of spheroids as previously cryopreserved and thawed HeLa and MCF-7 cells are cultured within a paper substrate according to Example IV.

In addition, 3D cell spheroids culture was performed after thawing the paper, without releasing the cells, to study cell functionality after cryopreservation. MCF-7 and HeLa cell spheroids were left in paper culture and allow to grow with respect to time after 1 day, after 3 days and after 6 days. FIG. 10 shows a graph representing increase in diameter of spheroids as there is increase in number of days in culture for HeLa and MCF-7 cells (Error bar represents duplicate experiments). The left column for each day corresponds to the diameter of the spheroids for for MCF cells. The right column for each day corresponds to the diameter of the spheroids for HeLa cells. It was also observed that the HeLa cells were unlocalized nor aggregated during seeding. This finding was also confirmed by confocal imaging (not shown), where spheroids were observed to increase their diameter over time in culture.

Example V

In Example V, MCF-7 cells were suspended in Matrigel (Corning, USA) and seeded on paper, cultured for 2 week. Cells were growing in layers on top and within the paper, forming 3D culture using Matrigel as scaffold and paper as scaffold and carrier. That was followed by cryopreservation, where the paper washed and loaded with freezing media (culture media+10% DMSO).

The paper was able to absorb the freezing media, hence, that give the cells appropriate freezing environment as the fibers holds the media, unlike many other culture scaffolds that cannot absorb the liquid. It was shown that 3D cultures of cells within Matrigel solution absorbed by the paper can be cryopreserved.

Example VI

In Example VI, filter paper was fabricated into 5×5 microarray of hydrophilic spots in a hydrophobic paper.

First, the paper was turned hydrophobic by vaporization of Trichloro (1H,1H,2H,2H-perfluorooctyl) silane (PFOTS). Next, the paper was patterned to form an array of hydrophilic regions by UV exposure through a 3D printed stencil (through-hole mask of 800 μm diameter). The backside surface of the paper was protected with scotch tape to keep it hydrophilic, thus enable cell culture medium penetration across the depth of the paper. The patterned array was characterized using food color dye, which shows selective hydrophobic-hydrophilic patterns. Selective exposure to UV allowed for forming hydrophilic regions for cell culture, which represents "virtual" paper-based microwells.

Figures 11A, 11B:
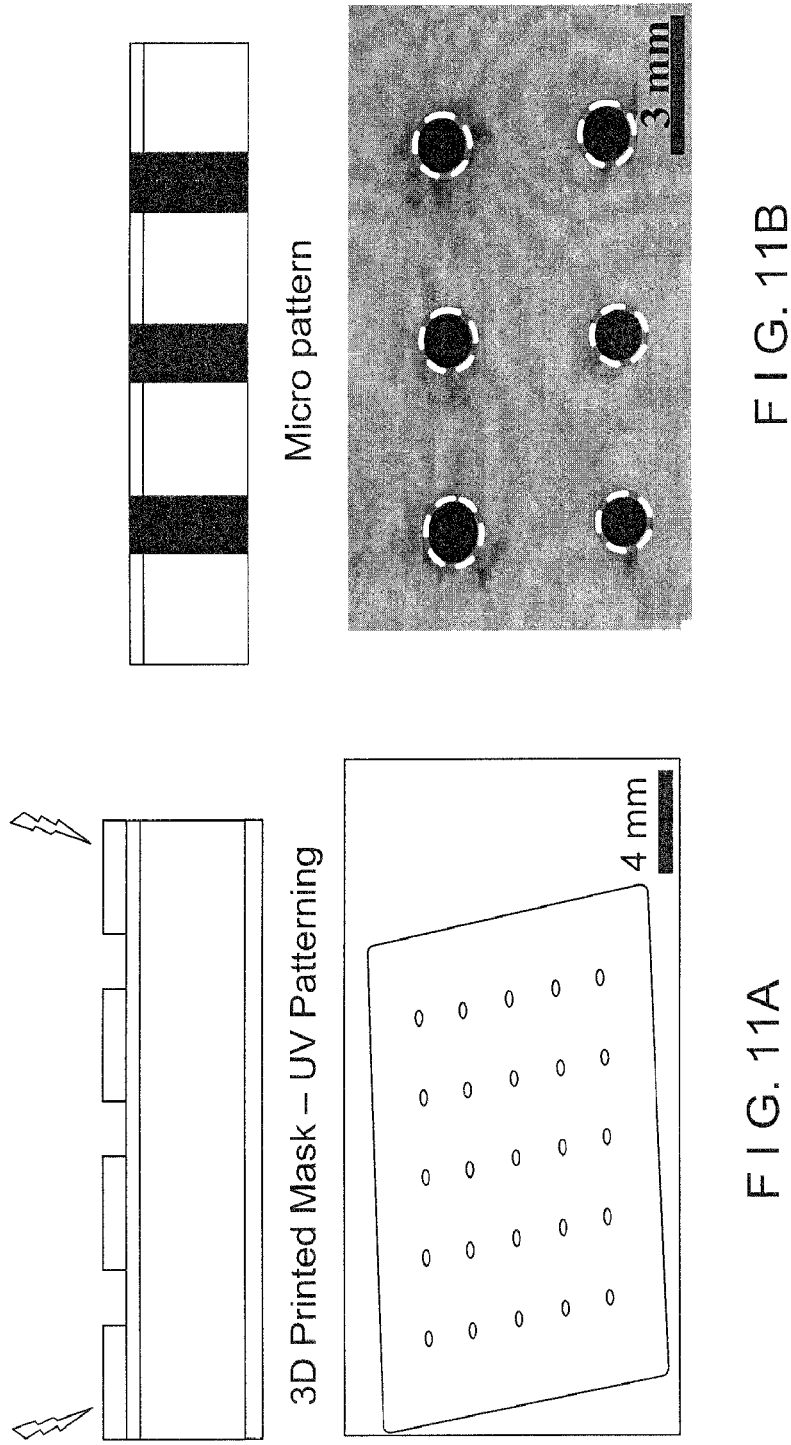
FIG. 11a shows an apparatus for localizing localize growth of spheroid structures within paper according to Example VI.
FIG. 11b shows fabrication of hydrophilic-hydrophobic regions on a paper platform using the apparatus of FIG. 11b.

FIGS. 11a and 11b show an apparatus for localizing growth of spheroid structures within paper. In particular, FIGS. 11a and 11b show fabrication of hydrophilic-hydrophobic regions on a paper platform. FIG. 11a provides a side-view schematics (top) and a representative diagram (bottom) of a 3D printed mask stencil (e.g., 800 μm well diameter, placed over the coated paper and exposed to UV Ozone for 16 minutes). FIG. 11b shows a side-view schematics (top) and a top-view diagram (bottom) of formed hydrophilic-hydrophobic micropattern using food dye.

The patterned paper was first coated with fibronectin, and then cells were seeded within the virtual paper-based microwells. Cells were left in culture for few days where spheroids formation was verified.

The examples provided herein provide cryopreservation methods that permit cells to be frozen in a paper platform with two choices, to be released or to be cultured. These cryopreservation methods may be further supported by a cell-release device and/or coating of the paper substrate with a protein from the extracellular matrix, such as fibronectin. The systems and methods of the present invention may be cost- and space-effective solutions for cell cryopreservation, and may provide a less time consuming method for 3D cell culture experiments.

The examples provided herein provide cryopreservation methods that permit 3D cultures of cells to be frozen in a paper platform with two choices, uniform 3D cultures or an array of 3D cell spheroids. These 3D cell cultures and cryopreservation methods may be further supported by mixing cell suspension with hydrogels or pattern the paper platform with hydrophobic-hydrophilic barriers for forming microarrays. The systems and methods of the present invention may be cost- and space-effective solutions for 3D cell cryopreservation.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A method for cryopreservation of mammalian cells, comprising:
obtaining a suspension of isolated mammalian cells in a cryopreservation medium comprising a cryoprotectant;
applying the suspension to a fibrous substrate comprising a network of interconnected cellulosic fibers defining a plurality of pores therein, the pores being sized to permit the suspension to absorb into the fibrous substrate such that the isolated mammalian cells penetrate and settle to an interior of the fibrous substrate; and cooling the fibrous substrate to or below a temperature of −80° C., wherein the mammalian cells are cultured within the fibrous substrate until formation of 3D mammalian cell cultures or spheroids prior to cooling the fibrous substrate and wherein a pattern of a hydrophilic agent is coated onto the fibrous substrate.

2. The method of claim 1, wherein the cryoprotectant is selected from a group consisting of glycerol, dimethyl sulfoxide (DMSO), and a combination thereof.

3. The method of claim 1, wherein an average diameter of the plurality of pores is from about 20 μm to about 200 μm.

4. The method of claim 1, wherein the cryopreservation medium comprises a hydrogel.

5. The method of claim 1, wherein the cryopreservation medium is free of a hydrogel.

6. The method of claim 1, wherein the fibrous substrate is paper.

7. The method of claim 1, wherein the fibrous substrate further comprises a glycoprotein of an extracellular matrix.

8. The method of claim 7, wherein the glycoprotein is fibronectin.

9. The method of claim 1, wherein the fibrous substrate further comprises a resin.

10. The method of claim 1, further comprising:
obtaining a suspension of isolated tumor cells in a cell culture medium comprising a cryoprotectant, wherein the cell culture medium is free of a hydrogel.

11. The method of claim 10, wherein the tumor cells may be selected from a group consisting of human cervical cancer cells, human breast cancer cells, human prostate cancer cells, and human seminoma cells.

12. The method of claim 1, wherein an average diameter of the plurality of pores from 100 μm to 150 μm.

13. The method of claim 1, wherein the suspension comprises isolated tumor cells in a concentration from $2 \times 10^3$ cell/mL to $1 \times 10^9$ cell/mL.

14. The method of claim 1, wherein a hydrophobic agent is coated onto a remainder of the fibrous substrate not coated by the hydrophilic agent.

15. The method of claim 1, wherein the mammalian cells are tumor cells.

16. The method of claim 1, wherein the pattern is an array of circular spots.

17. The method of claim 16, wherein the circular patterns have diameters from 50 μm to 1500 μm.

18. The method of claim 1, wherein the suspension comprises isolated tumor cells in a concentration from $2 \times 10^3$ cell/mL to $8 \times 10^3$.

* * * * *